US00PP12935P2

(12) United States Plant Patent
Vandenberg

(10) Patent No.: US PP12,935 P2
(45) Date of Patent: Sep. 10, 2002

(54) CHRYSANTHEMUM PLANT NAMED 'MOOD'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/757,509

(22) Filed: Jan. 11, 2001

(51) Int. Cl.[7] ..... A01H 5/00

(52) U.S. Cl. ..... Plt./290

(58) Field of Search ..... Plt./287, 289, 290

*Primary Examiner*—Howard J. Locker
(74) *Attorney, Agent, or Firm*—C. A. Whealy

(57) ABSTRACT

A distinct cultivar of Chrysanthemum plant named 'Mood', characterized by its large quilled decorative-type inflorescences that are about 13.8 cm in diameter; attractive golden bronze-colored ray florets; response time about 56 to 58 days; dark green foliage; strong stems; and good postproduction longevity with inflorescences maintaining good substance and color for about three to four weeks in an interior environment.

2 Drawing Sheets

BACKGROUND OF THE INVENTION

The present invention relates to a new and distinct cultivar of Chrysanthemum plant, botanically known as *Chrysanthemum×morifolium* and hereinafter referred to by the name 'Mood'.

The new Chrysanthemum is a product of a planned breeding program conducted by the Inventor in Salinas, Calif. and Alva, Fla. The objective of the breeding program is to create new cut Chrysanthemum cultivars having inflorescences with desirable colors and good form and substance.

The new Chrysanthemum originated from a cross made by the Inventor in January, 1994, in Salinas, Calif., of the Chrysanthemum cultivar Augusta, not patented, as the female, or seed, parent with a proprietary Chrysanthemum seedling selection identified as 1895, not patented, as the male, or pollen, parent.

The cultivar Mood was discovered and selected by the Inventor as a flowering plant within the progeny of the stated cross in a controlled environment in Alva, Fla., in November, 1996. The selection of this plant was based on its desirable inflorescence colors and good form and substance.

Asexual reproduction of the new Chrysanthemum by terminal cuttings taken in a controlled environment in Alva, Fla., has shown that the unique features of this new Chrysanthemum are stable and reproduced true to type in successive generations.

SUMMARY OF THE INVENTION

The cultivar Mood has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Mood'. These characteristics in combination distinguish 'Mood' as a new and distinct cultivar:

1. Large quilled decorative-type inflorescences that are about 13.8 cm in diameter.

2. Attractive golden bronze-colored ray florets.
3. Response time about 56 to 58 days.
4. Dark green foliage.
5. Thick and strong stems.
6. Good postproduction longevity with inflorescences maintaining good substance and color for about three to four weeks in an interior environment.

BRIEF DESCRIPTION OF THE PHOTOGRAPHS

The accompanying colored photographs illustrative the overall appearance of the new Chrysanthemum, showing the colors as true as it is reasonably possible to obtain in colored reproductions of this type. Colors in the photographs may differ slightly from the color values cited in the detailed botanical description which accurately describe the colors of the new Chrysanthemum.

The photograph on the first sheet comprises a side perspective view of a typical flowering stem of 'Mood' grown as a disbud-type cut Chrysanthemum.

The photograph at the top of the second sheet comprises a side perspective view of a typical flowering stem of 'Mood' grown as a spray-type cut Chrysanthemum.

The photograph at the bottom of the second sheet comprises a close-up view of typical inflorescences of 'Mood' grown as a spray-type (left) and as a disbud-type (right).

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate commercial practice in a double-layer polyethylene-covered greenhouse. Two-week old rooted cuttings were planted on Feb. 17, 2000 and received 11 long day/short nights followed by short day/long nights until flowering. Plants were grown as single-stem disbud-type cut chrysanthemums. During the production time, the following environmental conditions were measured: day temperatures, 18 to 27° C.; night temperatures, 16 to 18° C.; and light levels, 2,000 to 4,000 foot-candles. Measurements and numerical values represent averages for six to ten typical flowering stems and were taken during the week of Apr. 30, 2000.

Botanical classification: *Chrysanthemum×morifolium* cultivar Mood.

Commercial classification: Quilled decorative-type cut Chrysanthemum.

Parentage:

*Female or seed parent.*—*Chrysanthemum×morifolium* cultivar Augusta, not patented.

*Male or pollen parent.*—Proprietary *Chrysanthemum×morifolium* seedling selection identified as code number 1895, not patented.

Propagation:

*Type.*—Terminal tip cuttings.

*Time to rooting.*—Seven to ten days with soil temperatures of 21° C.

*Root description.*—Fine, fibrous and well-branched.

Plant description:

*Appearance.*—Herbaceous quilled decorative-type cut flower.

*Flowering stem description.*—Aspect: Erect. Length: About 99.1 cm. Diameter: About 8.5 mm. Internode length: About 4.7 cm. Texture: Pubescent. Color: Close to 146A.

*Foliage.*—description: Arrangement: Alternate. Length: About 11.4 cm. Width: About 7.6 cm. Apex: Cuspidate to mucronate. Base: Cuneate to truncate. Margin: Palmately lobed; sinuses mostly convergent and overlapping. Texture: Upper and lower surfaces pubescent; somewhat glossy; thick, rough and leathery, veins prominent on lower surface. Color: Young foliage upper surface: Much darker than 147A. Young foliage lower surface: Darker than 147B. Mature foliage upper surface: Darker than 147A; venation, close to 147A to 147B. Mature foliage lower surface: Close to 147B; venation, close to 147B. Petiole: Length: About 3.4 cm. Diameter: About 3.5 mm. Color: Close to 147B.

Flowering description:

*Appearance.*—Decorative-type inflorescence form with elongated quilled-shaped ray florets. Inflorescences borne on terminals, arising from leaf axils. Disc and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long nigh conditions flower about 56 days later when grown as a disbud-type and about 58 days later when grown as a spray-type.

*Postproduction longevity.*—In an interior environment, flowering stems will maintain good color and substance for about three to four weeks in an interior environment after one week of cool storage.

*Quantity of inflorescences.*—When grown as a spray-type, freely flowering with about 9 inflorescences per flowering stem. When grown as a disbud, one terminal inflorescence per flowering stem.

*Inflorescence size.*—Diameter: About 13.8 cm. Depth (height): About 4.9 cm. Diameter of disc: About 3.5 mm, inconspicious. Diameter of receptacle: About 1.2 cm.

*Ray florets.*—Shape: Elongated, quilled. Length: About 7.3 cm. Width: About 5 mm. Apex: Acute or emarginate. Base: Fused. Texture: Satiny, smooth, glabrous. Aspect: Initially incurved to mostly straight with upward curve towards apex; when mature, about 70 to 90° from vertical. Number of ray florets per inflorescence: About 337 arranged in numerous rows. Color: When opening, upper and lower surfaces: Yellow, 12A, overlain with grayed orange, 172A. Mature, inside and outside of tube: Yellow, 12A, overlain with grayed orange, 164A to 167A; towards base, mostly yellow, 12A.

*Disc florets.*—Shape: Tubular; slightly flared at apex. Length: About 7 mm. Width: Apex: About 2 mm. Base: About 1.5 mm. Number of disc florets per inflorescence: Few, massed at center of receptacle, typically about 7. Color: Immature: 144A. Mature: Apex: 9A. Mid-section and base: 155D.

*Peduncle* (*cut flowers grown as spray-type*).—Aspect: Strong, angled about 50 to 55° from vertical. Length: First peduncle: About 6.2 cm. Fourth peduncle: About 10.9 cm. Seventh peduncle: About 14.6 cm. Diameter: About 3 mm. Texture: Very fine pubescence. Color: 146A.

*Reproductive organs.*—Androecium: Present on disc florets only. Anther color: 9A. Amount of pollen: None observed. Gynoecium: Present on both ray and disc florets.

*Seed.*—Seed production has not been observed.

Disease resistance: Resistance to pathogens common to Chrysanthemums has not been observed on plants grown under commercial conditions.

Temperature tolerance: Plants of the new Chrysanthemum have demonstrated good tolerance to night temperatures as low as 5° C. and day temperatures lower than 40° C.

It is claimed:

1. A new and distinct cultivar of Chrysanthemum plant named 'Mood', as illustrated and described.

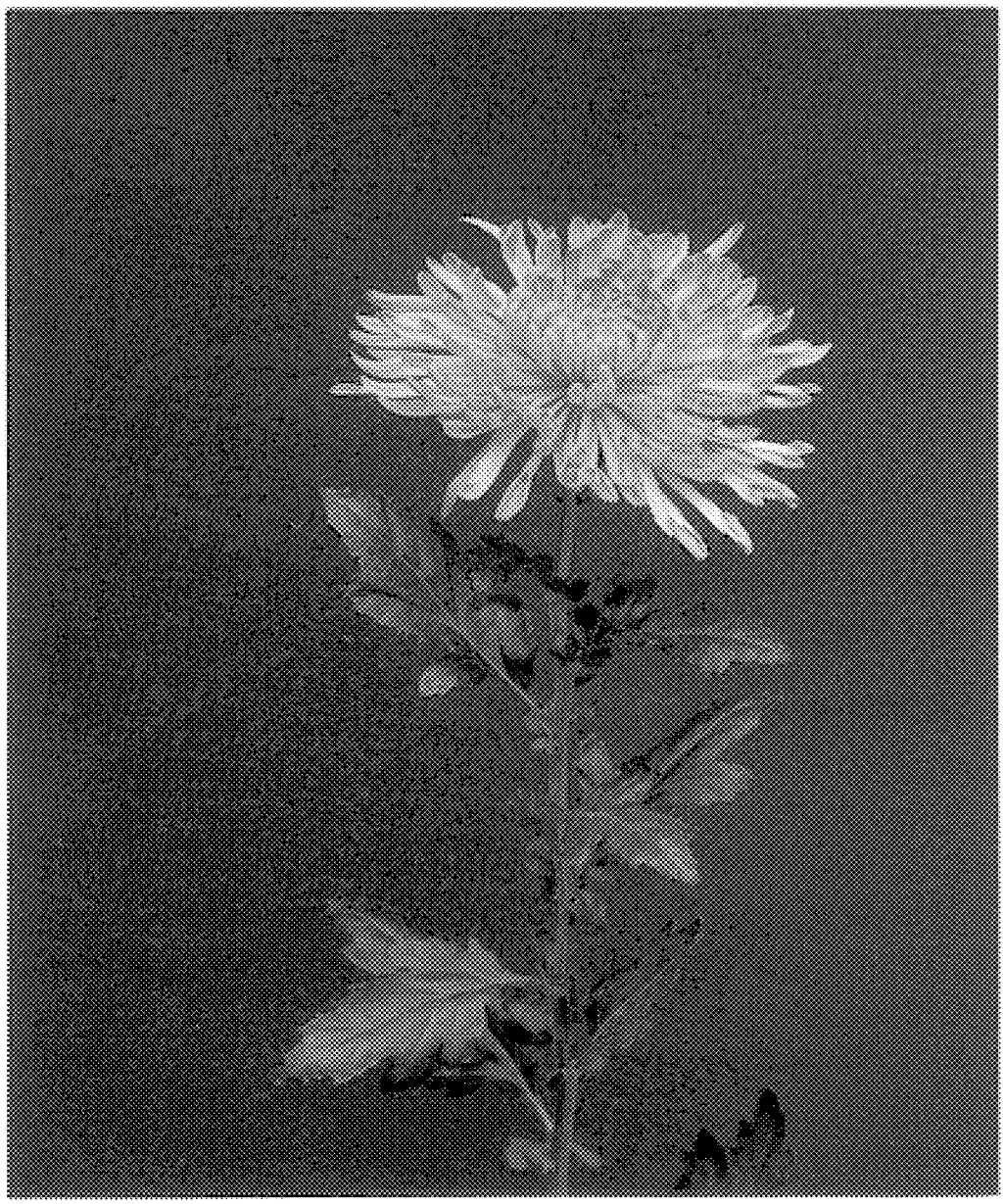

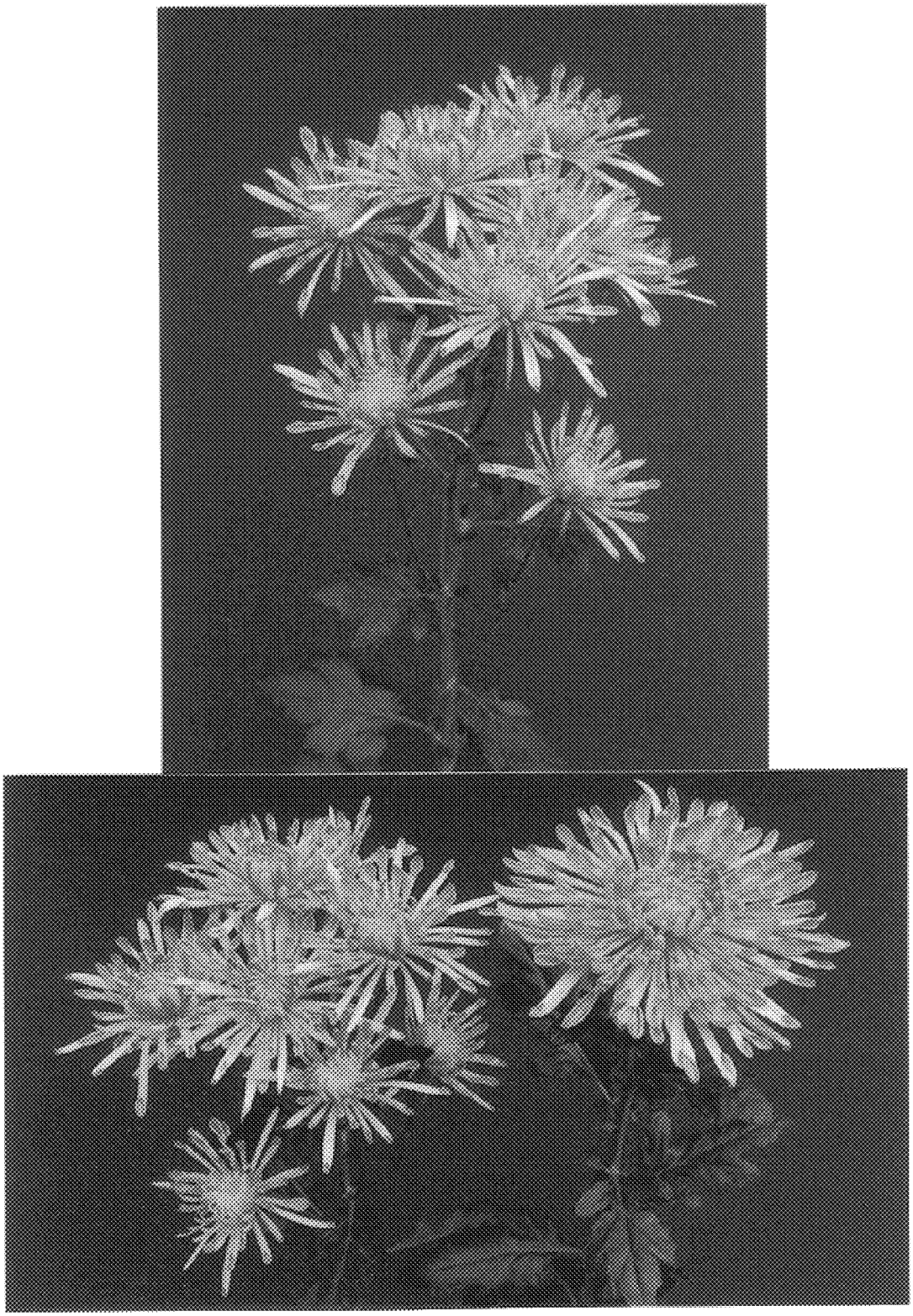

* * * * *